(12) United States Patent
Genova et al.

(10) Patent No.: US 11,000,339 B2
(45) Date of Patent: May 11, 2021

(54) SYSTEM AND APPARATUS FOR POSITIONING AN INSTRUMENT IN A BODY CAVITY FOR PERFORMING A SURGICAL PROCEDURE

(71) Applicant: Titan Medical Inc., Toronto (CA)

(72) Inventors: Perry A. Genova, Chapel Hill, NC (US); David McNally, Salt Lake City, UT (US)

(73) Assignee: Titan Medical Inc.

( * ) Notice: Subject to any disclaimer, the term of this patent is extended or adjusted under 35 U.S.C. 154(b) by 210 days.

(21) Appl. No.: 16/273,442

(22) Filed: Feb. 12, 2019

(65) Prior Publication Data

US 2019/0321118 A1 Oct. 24, 2019

Related U.S. Application Data

(63) Continuation of application No. 16/053,232, filed on Aug. 2, 2018, now Pat. No. 10,245,113, which is a
(Continued)

(51) Int. Cl.
*G06K 9/00* (2006.01)
*A61B 34/37* (2016.01)
(Continued)

(52) U.S. Cl.
CPC ............ *A61B 34/37* (2016.02); *A61B 1/0005* (2013.01); *A61B 1/00009* (2013.01);
(Continued)

(58) Field of Classification Search
None
See application file for complete search history.

(56) References Cited

U.S. PATENT DOCUMENTS 9,486,159 B2  11/2016  Coste-Maniere et al.
9,492,240 B2  11/2016  Itkowitz et al.
(Continued)

FOREIGN PATENT DOCUMENTS

WO   WO 2011/150376   12/2011
WO   WO 2015/149046   10/2015
WO   WO 2017/124177    1/2017

OTHER PUBLICATIONS

U.S. Appl. No. 16/053,232, filed Aug. 2, 2018, Genova et al.

*Primary Examiner* — Atiba O Fitzpatrick
(74) *Attorney, Agent, or Firm* — Knobbe, Martens, Olson & Bear, LLP

(57) ABSTRACT

Methods and systems for insertion of an instrument into a body cavity of an animal for performing a surgical procedure using a processor circuit controlled robotic surgery system are disclosed. In some embodiments, a method involves receiving body cavity image data representing an interior view of the body cavity captured by a camera inserted into the body cavity, determining, by the processor circuit, instrument parameters associated with physical extents of the instrument to be inserted, determining, by the processor circuit, an instrument envelope identifying a region through which the instrument is capable of moving in the body cavity, and generating, by the processor circuit, display signals operable to display a composite view of the interior of the body cavity on a display, the composite view being based on the body cavity image data and including an envelope overlay image generated to represent the instrument envelope.

24 Claims, 10 Drawing Sheets

Related U.S. Application Data continuation of application No. 15/961,507, filed on Apr. 24, 2018, now Pat. No. 10,058,396.

(51) Int. Cl.

| | | |
|---|---|---|
| *G06T 7/70* | (2017.01) | |
| *A61B 34/20* | (2016.01) | |
| *A61B 90/00* | (2016.01) | |
| *A61B 1/00* | (2006.01) | |
| *A61B 1/313* | (2006.01) | |
| *A61B 34/00* | (2016.01) | |
| *A61B 17/02* | (2006.01) | |
| *G06T 7/73* | (2017.01) | |
| *A61B 34/30* | (2016.01) | |
| *A61B 34/10* | (2016.01) | |
| *A61B 90/30* | (2016.01) | |

(52) U.S. Cl.
CPC .......... *A61B 1/00149* (2013.01); *A61B 1/313* (2013.01); *A61B 17/02* (2013.01); *A61B 34/20* (2016.02); *A61B 34/74* (2016.02); *A61B 90/37* (2016.02); *G06T 7/70* (2017.01); *G06T 7/73* (2017.01); *A61B 34/10* (2016.02); *A61B 34/25* (2016.02); *A61B 90/03* (2016.02); *A61B 2034/2057* (2016.02); *A61B 2034/2065* (2016.02); *A61B 2034/302* (2016.02); *A61B 2090/306* (2016.02); *A61B 2090/309* (2016.02); *A61B 2090/371* (2016.02); *G06T 2207/10021* (2013.01); *G06T 2207/30004* (2013.01)

(56) References Cited

U.S. PATENT DOCUMENTS

| | | |
|---|---|---|
| 9,516,996 B2 | 12/2016 | Diolaiti et al. |
| 10,058,396 B1 | 8/2018 | Genova et al. |
| 2004/0068173 A1 | 4/2004 | Viswanathan |
| 2005/0182295 A1 | 8/2005 | Soper et al. |
| 2006/0064010 A1 | 3/2006 | Cannon, Jr. et al. |
| 2009/0326318 A1 | 12/2009 | Tognaccini et al. |
| 2011/0295108 A1 | 12/2011 | Cox et al. |
| 2014/0081127 A1 | 3/2014 | Patil et al. |
| 2018/0132944 A1* | 5/2018 | Yan .......................... G06T 7/12 |
| 2018/0161063 A1 | 6/2018 | Miyake |
| 2019/0192232 A1* | 6/2019 | Altmann ................ A61B 5/066 |

* cited by examiner

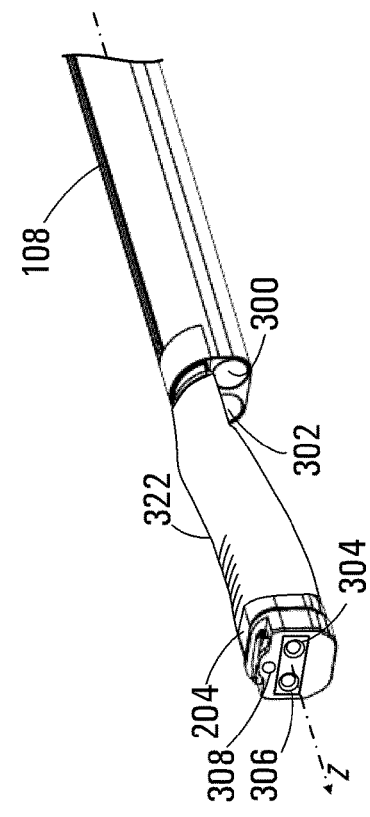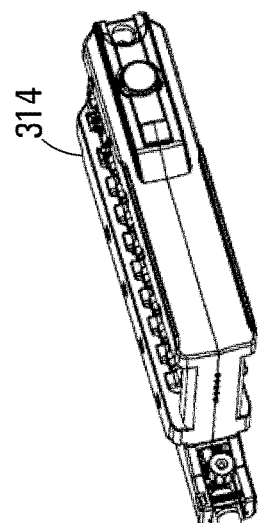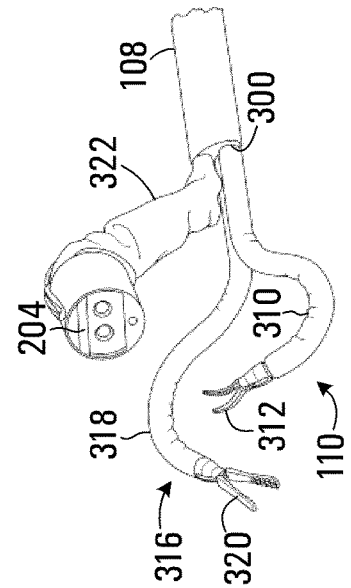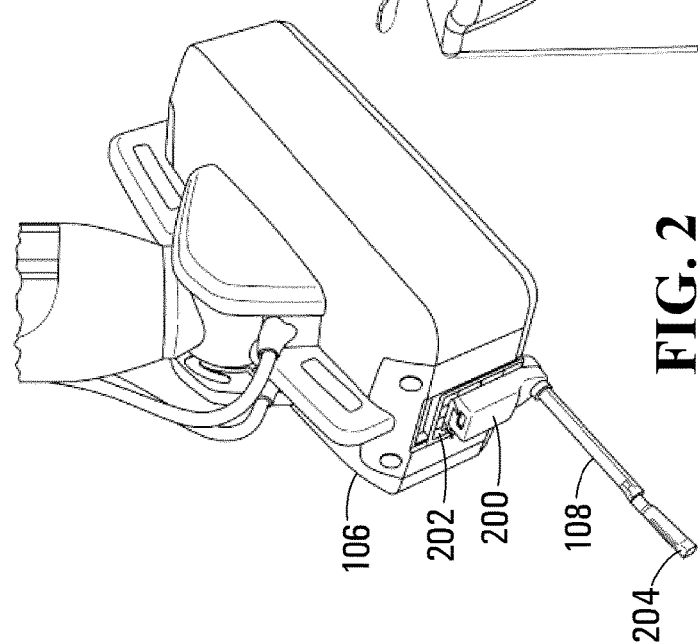

SYSTEM AND APPARATUS FOR POSITIONING AN INSTRUMENT IN A BODY CAVITY FOR PERFORMING A SURGICAL PROCEDURE

BACKGROUND

1. Field

This disclosure relates generally to robotic surgery systems and more particularly to insertion of an instrument into a body cavity of a patient for performing a surgical procedure using the robotic surgery system.

2. Description of Related Art

When performing surgery using a robotic surgical system, instruments are usually inserted into a body cavity of a patient. The insertion process has some risk since instruments may inadvertently damage organs and/or tissue while being inserted. Incorrect positioning of the instruments in the body cavity may also result in a limited range of motion within the body cavity.

As an example, when performing abdominal surgery, at least one incision would be made in a body wall of the patient's abdomen. A trocar, or other access port, may then be inserted through the incision. In many cases a camera is first inserted through the access port and used by the surgeon to capture and relay stereoscopic images of the surgical site. Instruments are usually inserted following the camera insertion. Views provided by the camera facilitate it's positioning to focus on the surgical site, however it may not be evident to the surgeon how far the instruments will extend into the body cavity when inserted. For example, scaling of the views provided by the camera may lead to the mistaken belief that there is more clearance from sensitive anatomy than actually available. The surgeon may thus only be able to determine the depth to which the instrument will extend into the body cavity based on an educated guess. In some cases the camera and/or instruments may be positioned such that a surgical workspace within which the instruments are capable of reaching is less than optimal. There remains a need for methods and systems that address these issues and provide information associated with the instrument insertion and positioning process at the outset and/or during the surgery.

SUMMARY

In accordance with some embodiments there is provided a method for controlling insertion of an instrument into a body cavity of an animal for performing a surgical procedure using a robotic surgery system, the robotic surgery system being controlled by a processor circuit. The method involves, by the processor circuit, receiving body cavity image data, the body cavity image data being captured by a camera inserted into the body cavity and representing an interior view of the body cavity and determining instrument parameters associated with physical extents of the instrument to be inserted into the body cavity. The method further involves determining by the processor circuit an instrument envelope based on the instrument parameters, the instrument envelope identifying a region through which the instrument is capable of moving when inserted into the body cavity. The method also involves generating by the processor circuit display signals operable to display a composite view of the interior of the body cavity on a display associated with the robotic surgery system, the composite view being based on the body cavity image data and including an envelope overlay image generated to represent the instrument envelope.

Determining the instrument envelope may involve determining an instrument envelope identifying a region through which the instrument is capable of physically moving when inserted into the body cavity.

Determining the instrument envelope may involve determining a physical reach of the instrument in at least one degree of freedom associated with the instrument prior to insertion of the instrument into the body cavity.

Receiving the body cavity image data may involve receiving body cavity image data including three-dimensional spatial information, and processing the body cavity image data may involve processing the body cavity image data to determine a three-dimensional instrument envelope.

Generating display signals may involve generating three-dimensional display signals operable to display a three-dimensional composite view of the interior of the body cavity on a three-dimensional display device associated with the robotic surgery system.

Receiving the body cavity image data may involve receiving body cavity image data from at least one of a stereoscopic camera including a pair of image sensors each image sensor being operably configured to capture an image of the interior of the body cavity from a different perspective to facilitate determination of the three-dimensional spatial information, a time of flight camera operably configured to generate image data including the three-dimensional spatial information, or a camera in combination with a structured light source for illuminating the interior of the body cavity to facilitate determination of the three-dimensional spatial information.

Processing the body cavity image to determine the instrument envelope may be based on determining an anticipated insertion location and orientation for the instrument relative to the camera.

Determining the anticipated insertion location and orientation for the instrument may involve generating the location and orientation as an offset with respect to the camera based on the instrument parameters.

The camera may be coupled to a first manipulator and the instrument may be coupled to a second manipulator, the first and second manipulators being associated with the robotic surgery system and the method may further involve determining a spatial disposition of the camera and determining the anticipated insertion location and orientation for the instrument by receiving kinematic information associated with the first and second manipulators and determining the anticipated insertion location and orientation for the instrument as offsets from the respective orientations and locations of the first and second manipulators.

The instrument parameters may provide information for determining a possible physical extent of the instrument into the body cavity.

The camera may be initially detached from the robotic surgery system facilitating positioning of the camera by hand to receive a desired interior view of the body cavity based on the composite view and the method may further involve connecting the camera to the robotic surgery system once the positioning is completed to facilitate further positioning of the camera by the processor circuit.

The method may involve discontinuing display of the envelope overlay image following actual insertion of the instrument into the body cavity.

The method may involve process by the processor circuit the body cavity image data to identify anatomical features in the image data and the composite view may further include an anatomical overlay image generated to identify at least one anatomical feature within the body cavity.

The anatomical overlay image may include a highlighted region within the body cavity image identifying at least one anatomical feature.

The method may involve determining by the processor circuit whether there are any regions of potential encroachment between the instrument envelope and identified anatomical features and generating an alert signal in response to identifying a region of potential encroachment.

Generating the alert signal may involve generating a warning overlay image for display as part of the composite image.

The camera may be coupled to a drive unit operable to move the camera within the body cavity and may further involve inhibiting further movement of the drive unit in response to the alert signal.

The camera may be disposed in a longitudinally extended state when inserted into the body cavity and subsequently moved into a deployed state for performing the surgical procedure, and the composite view may be generated based on images captured by the camera in the longitudinally extended state including a first perspective, the composite image being further transformed for display to include a second perspective that generally corresponds to a perspective of the camera in the deployed state.

Determining the instrument envelope may involve determining an instrument envelope identifying a workable volume within which the instrument is capable of manipulating.

In accordance with some embodiments there is provided a robotic surgery system. The system includes a camera configured to be inserted into a body cavity of an animal to capture body cavity image data representing an interior view of the body cavity and a processor circuit for controlling the robotic surgery system, the processor circuit being operably configured to receive the body cavity image data. The system further includes an instrument for performing a surgical procedure within the body cavity when received in the body cavity. The processor circuit is operably configured to determine instrument parameters associated with physical extents of the instrument to be inserted into the body cavity, and to determine an instrument envelope based on the instrument parameters, the instrument envelope identifying a region through which the instrument is capable of moving when inserted into the body cavity. The processor circuit is also operably configured to generate display signals operable to display a composite view of the interior of the body cavity, the composite view being based on the body cavity image data and including an envelope overlay image generated to represent the instrument envelope. The processor circuit is further operably configured to display associated with the robotic surgery system operably configured to receive the display signals and to display the composite view.

The processor circuit may be operably configured to determine the instrument envelope by determining an instrument envelope identifying a region through which the instrument is capable of physically moving when inserted into the body cavity.

The processor circuit may be operably configured to determine the instrument envelope by determining a physical reach of the instrument in at least one degree of freedom associated with the instrument prior to insertion of the instrument into the body cavity.

The processor circuit may be operably configured to receive the body cavity image data by receiving body cavity image data including three-dimensional spatial information and the processor circuit may be operably configured to process the body cavity image data to determine a three-dimensional instrument envelope.

The processor circuit may be operably configured to generate display signals by generating three-dimensional display signals operable to display a three-dimensional composite view of the interior of the body cavity on a three-dimensional display device associated with the robotic surgery system.

The processor circuit may be operably configured to receive body cavity image data from at least one of a stereoscopic camera including a pair of image sensors each image sensor being operably configured to capture an image of the interior of the body cavity from a different perspective to facilitate determination of the three-dimensional spatial information, a time of flight camera operably configured to generate image data including the three-dimensional spatial information, or a camera in combination with a structured light source for illuminating the interior of the body cavity to facilitate determination of the three-dimensional spatial information.

The processor circuit may be operably configured to process the body cavity image to determine the instrument envelope by determining the instrument envelope based on determining an anticipated insertion location and orientation for the instrument relative to the camera.

The processor circuit may be operably configured to determine the anticipated insertion location and orientation for the instrument by generating the location and orientation as an offset with respect to the camera based on the instrument parameters.

The camera may be coupled to a first manipulator and the instrument may be coupled to a second manipulator, the first and second manipulators being associated with the robotic surgery system and the processor circuit may be operably configured to determine a spatial disposition of the camera and determine the anticipated insertion location and orientation for the instrument by receiving kinematic information associated with the first and second manipulators and to determine the anticipated insertion location and orientation for the instrument as offsets from the respective orientations and locations of the first and second manipulators.

The instrument parameters may provide information for determining a possible physical extent of the instrument into the body cavity.

The robotic surgery system may be operably configured to permit the camera to be initially detached from the system facilitating positioning of the camera by hand to receive a desired interior view of the body cavity based on the composite view and the system may be further operably configured to facilitate connecting the camera to the robotic surgery system once the positioning is completed to facilitate further positioning of the camera by the processor circuit.

The processor circuit may be operably configured to discontinue display of the envelope overlay image following actual insertion of the instrument into the body cavity.

The processor circuit may be operably configured to process the body cavity image data to identify anatomical features in the image data and the composite view generated by the processor circuit may further include an anatomical overlay image generated to identify at least one anatomical feature within the body cavity.

The anatomical overlay image may include a highlighted region within the body cavity image identifying at least one anatomical feature.

The processor circuit may be operably configured to determine whether there are any regions of potential encroachment of between the instrument envelope and identified anatomical features and to generate an alert in response to identifying a region of potential encroachment.

The processor circuit may be operably configured to generate the alert by generating a warning overlay image for display as part of the composite image.

The camera may be coupled to a drive unit operable to move the camera within the body cavity and the processor circuit may be operably configured to inhibit further movement of the drive unit in response to the alert signal.

The camera may be disposed in a longitudinally extended state when inserted into the body cavity and subsequently moved into a deployed state for performing the surgical procedure, and the processor circuit may be operably configured to generate the composite view based on images captured by the camera in the longitudinally extended state including a first perspective and to transform the composite image for display to include a second perspective that generally corresponds to a perspective of the camera in the deployed state.

The processor circuit may be operably configured to determine the instrument envelope by determining an instrument envelope identifying a workable volume within which the instrument is capable of manipulating.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments,

FIG. 2 is a perspective view of a drive unit and insertion tube of the robotic surgery system shown in FIG. 1;

FIG. 3A is a perspective view of a portion of the insertion tube shown in FIG. 2 and a camera disposed on an end of the insertion tube;

FIG. 3B is a perspective view of the insertion tube and an instrument being inserted through the insertion tube;

FIG. 3C is a perspective view of the insertion tube and instruments with the camera in a deployed state;

FIG. 15B is an example of a view generated by the processor circuit for the camera position shown in

FIG. 14A;

DETAILED DESCRIPTION

Figure 1:
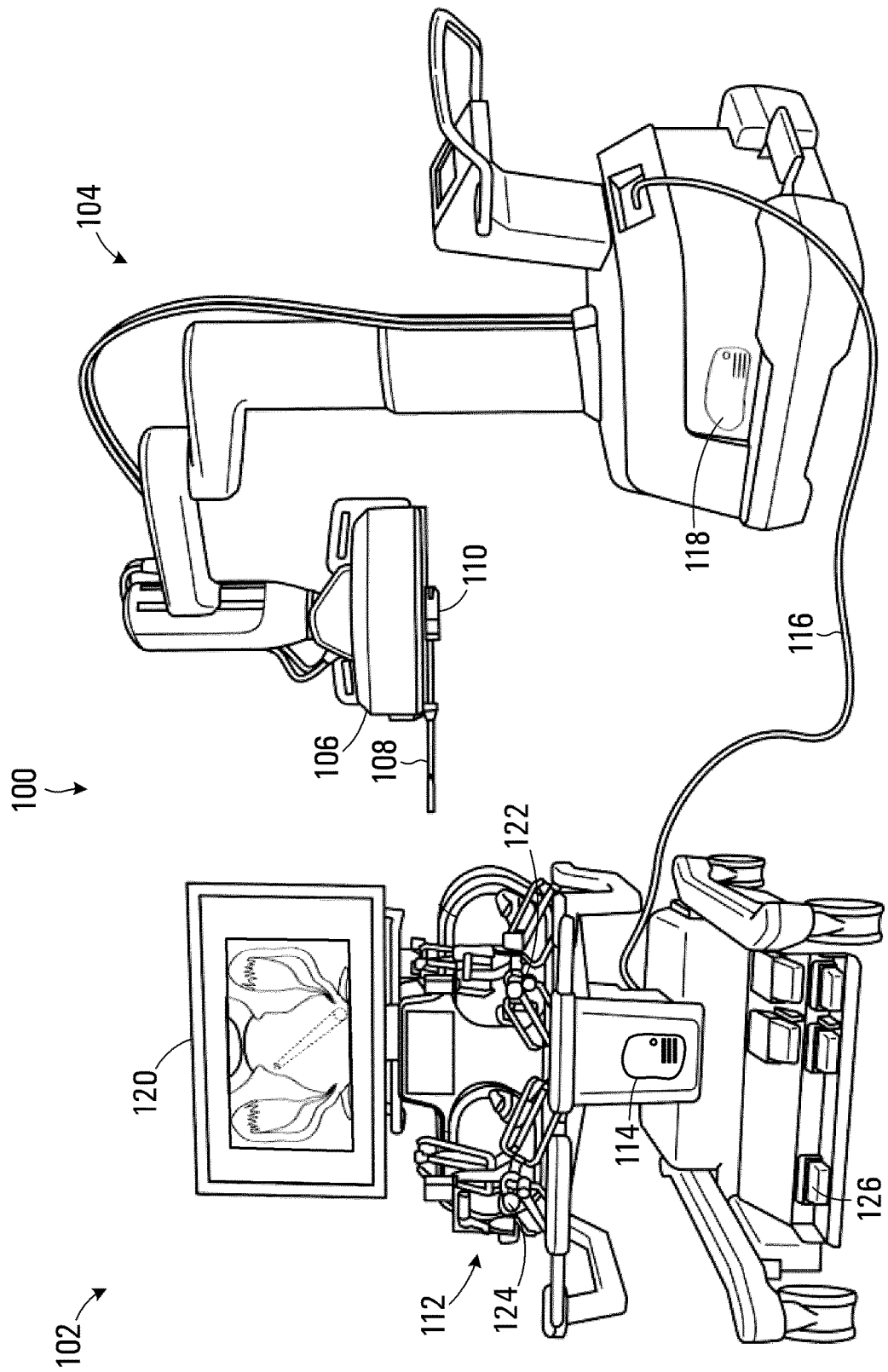
FIG. 1 is a perspective view of a robotic surgery system in accordance with some embodiments.

Referring to FIG. 1, a robotic surgery system in accordance with some embodiments is shown generally at 100. The system 100 includes a workstation 102 and an instrument cart 104. The instrument cart 104 includes a drive unit 106 to which an insertion tube 108 and an instrument 110 are mounted. The workstation 102 includes an input device 112 that receives operator input and produces input signals and may also be capable of generating haptic feedback to the operator. The input device 112 may be implemented using a haptic interface available from Force Dimension, of Switzerland, for example. In the embodiment shown, the workstation 102 further includes a master processor circuit 114 in communication with the input device 112 for receiving the input signals and generating control signals for controlling the robotic surgery system, which are transmitted to the instrument cart 104 via an interface cable 116. The input device 112 includes right and left hand controllers 122 and 124, which are grasped by the operator's hands and moved to produce input signals at the input device. The instrument cart 104 includes a slave processor circuit 118 that receives and the control signals from the master processor circuit 114 and produces slave control signals operable to control the insertion tube 108 and the instrument 110 during a surgical procedure. While the embodiment shown includes both master and slave processor circuits, in other embodiments a single processor circuit may be used to perform both master and slave functions. The workstation 102 also includes a display 120 in communication with the master processor circuit 114 for displaying body cavity images and other information to an operator.

The drive unit 106 is shown in isolation in FIG. 2. Referring to FIG. 2, the insertion tube 108 includes a drive interface 200 that detachably mounts to a corresponding drive interface 202 on the drive unit 106. The insertion tube 108 includes a camera 204 at a distal end of the insertion tube. The camera 204 is operably configured to be inserted into a body cavity of a patient to capture body cavity image data representing an interior view of the body cavity.

Referring to FIG. 3, a portion of the insertion tube 108 is shown in FIG. 3A and includes two adjacently located bores 300 and 302 extending through the insertion tube 108 for receiving a surgical instrument. The camera 204 is configured as a stereoscopic camera having a pair of spaced apart imagers 304 and 306 for producing stereoscopic views representing an interior view of the body cavity. The camera 204 also includes an illumination source 308 for illuminating the body cavity for capturing images. The illumination source 308 may be implemented locally on the camera using a light emitting diode or the illumination source may be remotely located and may deliver the illumination through an optical fiber running through the insertion tube 108.

The insertion tube 108 is shown isolated from the drive unit 106 in FIG. 3B. Referring to FIG. 3B, the instrument 110 is partially inserted through the bore 300 and includes a manipulator 310 and an end effector 312 at a distal end of the instrument. The manipulator 310 may include an articulated tool positioner as described in detail in commonly owned PCT patent publication WO2014/201538 entitled "ARTICULATED TOOL POSITIONER AND SYSTEM EMPLOYING SAME" filed on Dec. 20, 2013 and incorporated herein by reference in its entirety. The described manipulator in PCT patent publication WO2014/201538 provides for dexterous movement of the end effector 312 through a plurality of articulated segments. The end effector 312 may be any of a variety of tools generally used in laparoscopic surgery such as surgical scissors, forceps, and/or an electrocauterization tool. In this embodiment the instrument 110 includes an actuator 314 at a proximal end of the instrument that couples to a corresponding interface (not shown) on the drive unit 106 for manipulating the instrument. The instrument 110 and the actuator 314 may be configured as disclosed in commonly owned PCT patent publication WO2016/090459 entitled "ACTUATOR AND DRIVE FOR MANIPULATING A TOOL" filed on Feb. 18, 2015 and incorporated herein by reference in its entirety. The interface of the drive unit 106 may have a track system (not shown) for advancing and retracting the actuator 314 through the bore 300 in response to the input signals received from the input device 112 to place the end effector 312 at a desired longitudinal offset with respect to the insertion tube 108.

When the insertion tube 108 is detached as shown in FIG. 3A, the camera 204 remains in a longitudinally extended or in-line state generally oriented along a longitudinal z-axis of the insertion tube 108. The camera 204 is mounted on an articulated arm 322 moveable in response to drive forces delivered by the drive interface 202 of the drive unit 106 to the drive interface 200 of the insertion tube 108. The articulated arm 322 may be covered by a sterile boot that encloses the articulating mechanism. In some embodiments the articulated arm 322 may be configured as disclosed in commonly owned PCT patent publication WO 2017/173524 entitled "Camera Positioning Method and Apparatus for Capturing Images during a Medical Procedure", filed on Apr. 4, 2017 and incorporated herein by reference in its entirety. When the arm 322 is actuated to move the camera 204, the actuation provided may be used to determine the relative positioning of the camera within the surgical workspace.

The drive forces delivered by the drive unit 106 cause the camera 204 to move from the longitudinally extended insertion state shown in FIGS. 3A and 3B to a deployed state as shown in FIG. 3C. Further when drive forces are imparted on the actuator 314 by the drive unit 106, the manipulator 310 of the instrument 110 is actuated to perform dexterous movement to position the end effector 312 for performing various surgical tasks. As shown in FIG. 3C, a second instrument 316 is also inserted for performing surgical tasks. The second instrument 316 may be similarly configured to the instrument 110, thus having a manipulator 318 and an end effector 320. In the deployed position shown in FIG. 3C, the camera 204 is able to generate images of the body cavity without obstructing movements of the manipulators 310 and 318.

Figure 4:
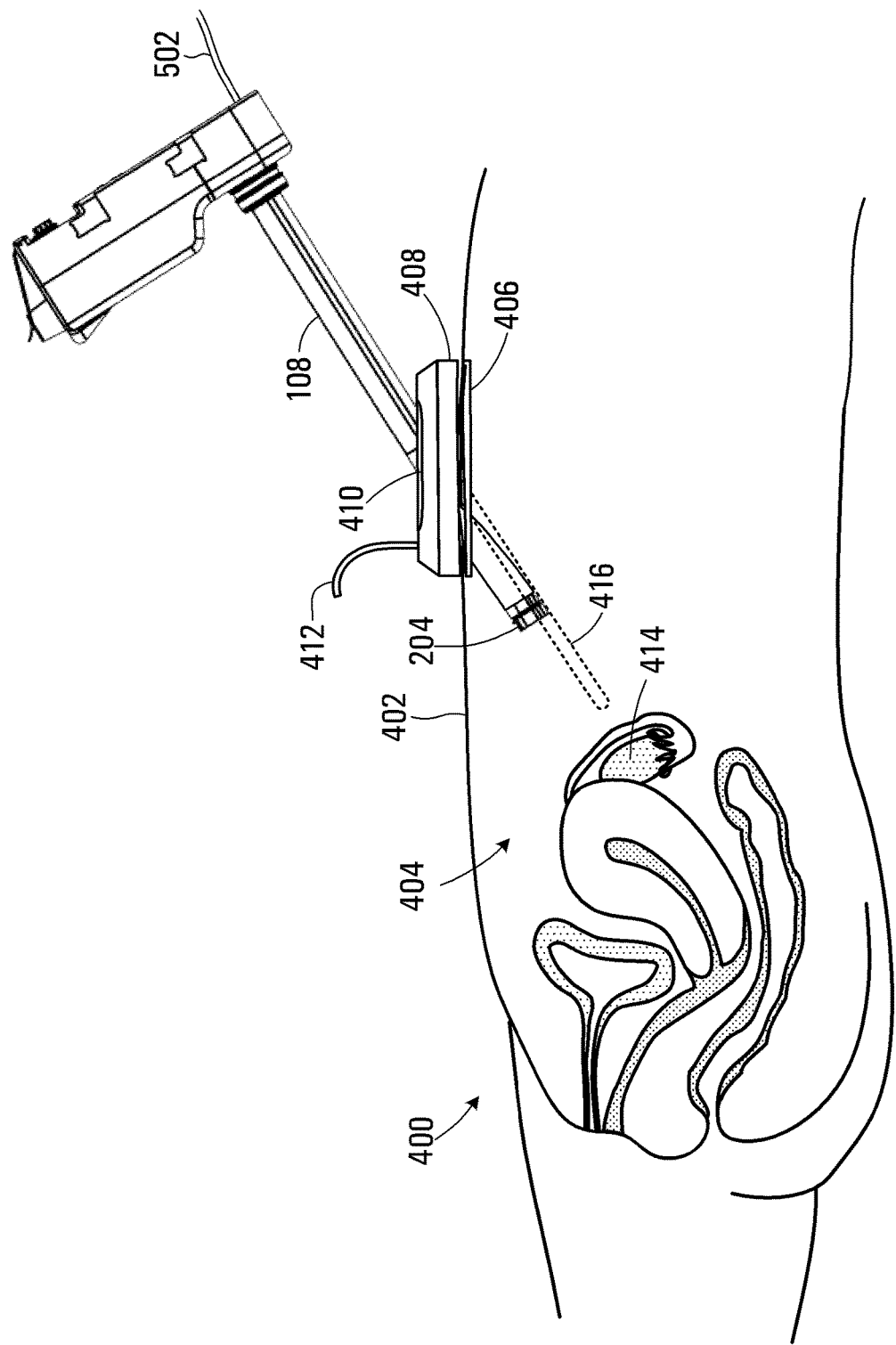
FIG. 4 is a sectional view of a patient's abdomen with the insertion tube inserted into a body cavity.

Referring to FIG. 4, at the commencement of a surgical procedure a patient 400 may have had an incision made in a wall 402 of the patient's abdomen or other body region to provide access to an underlying body cavity 404. In the embodiment shown, a wound retractor 406 has been inserted and a cap 408 attached to the underlying wound retractor to provide a seal and a point of entry into the body cavity 404. The insertion tube 108 and camera 204 are initially detached from the drive unit 106, and with no instrument 110 loaded at the commencement of a surgical procedure, may be manually inserted through an opening 410 in the cap 408. This facilitates positioning of the camera 204 by hand to receive a desired interior view of the body cavity 404 and ensure that there are no obstructions within the body cavity 404. The cap 408 includes an inlet for receiving a fluid flow from an insufflation line 412. Insufflation of the abdominal body cavity with a gas such as carbon dioxide distends the abdomen providing for entry and sufficient operating space for manipulation of surgical instruments during the surgical procedure. In other embodiments the insertion tube 108 may be inserted into a body cavity via a natural bodily orifice, i.e. a transanal, transvaginal, or transoral insertion, for example.

The insertion tube 108 may be initially detached from the drive unit 106 for insertion into a body cavity 404 of the patient 400, but coupled via an image signal line 502 to the slave processor circuit 118 such that images of the interior of the body cavity 404 can be displayed on the display 120. At the time of insertion of the insertion tube 108 through the cap 408, neither of the instruments 110 or 316 (shown in FIG. 3C) is initially received through the respective bores 300 and 302. The end effectors 312 and 320 on the instruments 110 and 316 may have sharp cutting edges and are not initially introduced into the body cavity 404 due to the risk of causing damage to tissue prior to the camera 204 being able to capture and relay body cavity image data back to the master processor circuit 114. The cap 408 has sufficient compliance to permit the camera 204 to be moved around within the body cavity 404 and aligned to cause the illumination source 308 (shown in FIG. 3A) to illuminate a desired region of the body cavity 404 for capturing images of the patient's anatomy. The camera 204 thus captures body cavity image data, which is relayed back via the slave processor circuit 118 to the master processor circuit 114 for display on the display 120 of the workstation 102.

Figure 5:
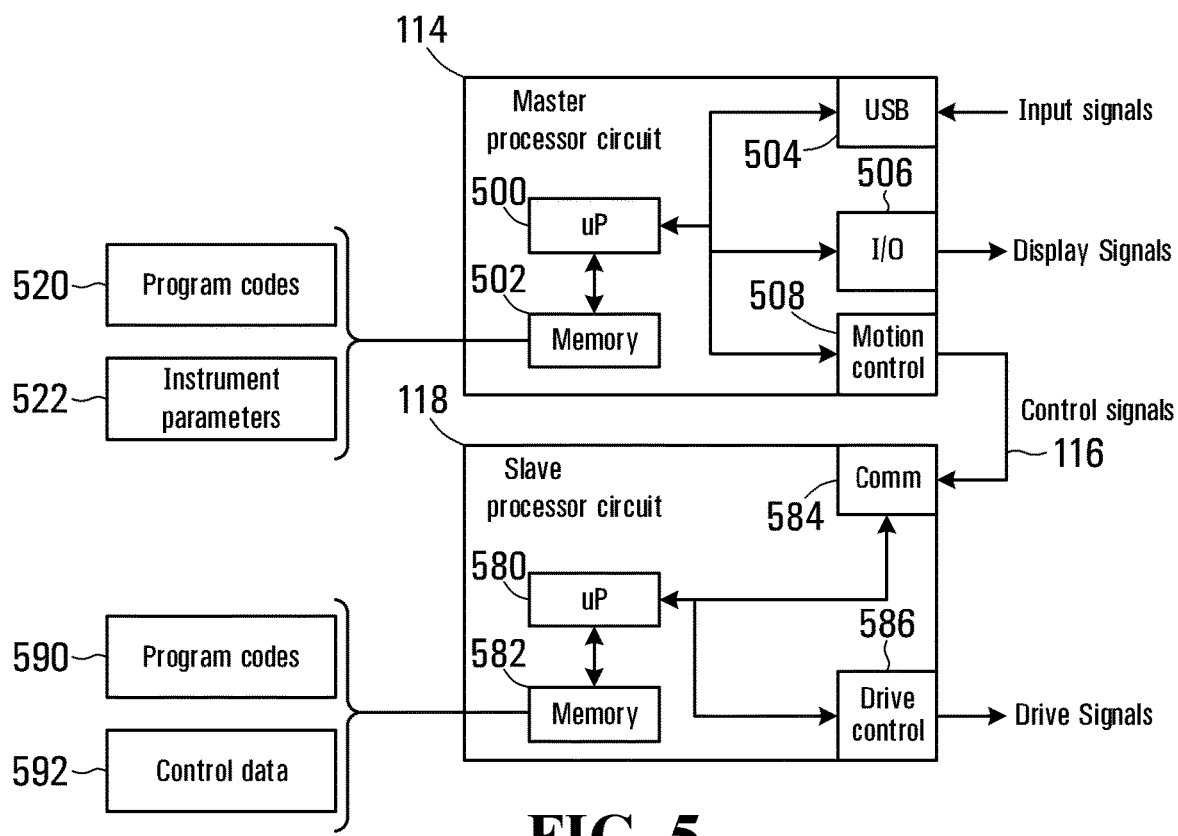
FIG. 5 is a block diagram of processor circuit elements of the system shown in FIG. 1.

A block diagram of the processor circuit elements of the system 100 is shown in FIG. 5. Referring to FIG. 5 the master processor circuit 114 on the workstation 102 includes a microprocessor 500, a memory 502, a USB interface 504, an input/output 506 and a motion control interface 508, all of which are in communication with the microprocessor 500. In this embodiment the input device 112 (shown in FIG. 1) communicates using a USB protocol and the USB interface 504 receives input signals produced by the input device in response to movements of the hand controllers 122 and 124. The microprocessor 500 processes the input signals and causes the motion control interface 508 to transmit control signals to the instrument processor circuit 118 via the interface cable 116. The memory 502 provides storage for program codes 520 for directing the microprocessor 500 to perform various functions. The memory 502 also includes storage for data, such as instrument parameters 522.

The slave processor circuit 118 on the instrument cart 104 includes a microprocessor 580, a memory 582, a communications interface 584, and a drive control interface 586, all of which are in communication with the microprocessor. The microprocessor 580 receives the control signals at the communications interface 584 over the interface cable 116 from the master processor circuit 114 of the workstation 102. The microprocessor 580 then processes the control signals, which are output by the drive control interface 586 and cause the drive unit 106 to produce drive forces for moving the instruments 110 and 316 and the camera 204. The memory 582 provides storage for program codes 590 and other control data 592 associated with operation of the instrument cart 104.

The master processor circuit 114 acts as a master subsystem for receiving operator input from the input device 112, while the slave processor circuit 118, drive unit 106 and instrument 110 act as a slave subsystem in responding to the operator input. In other embodiments, functions performed by the master and slave processor circuits 114 and 118 may be performed by a single processor circuit, operably configured to both receive the input signals and generate the drive signals.

Figure 6:
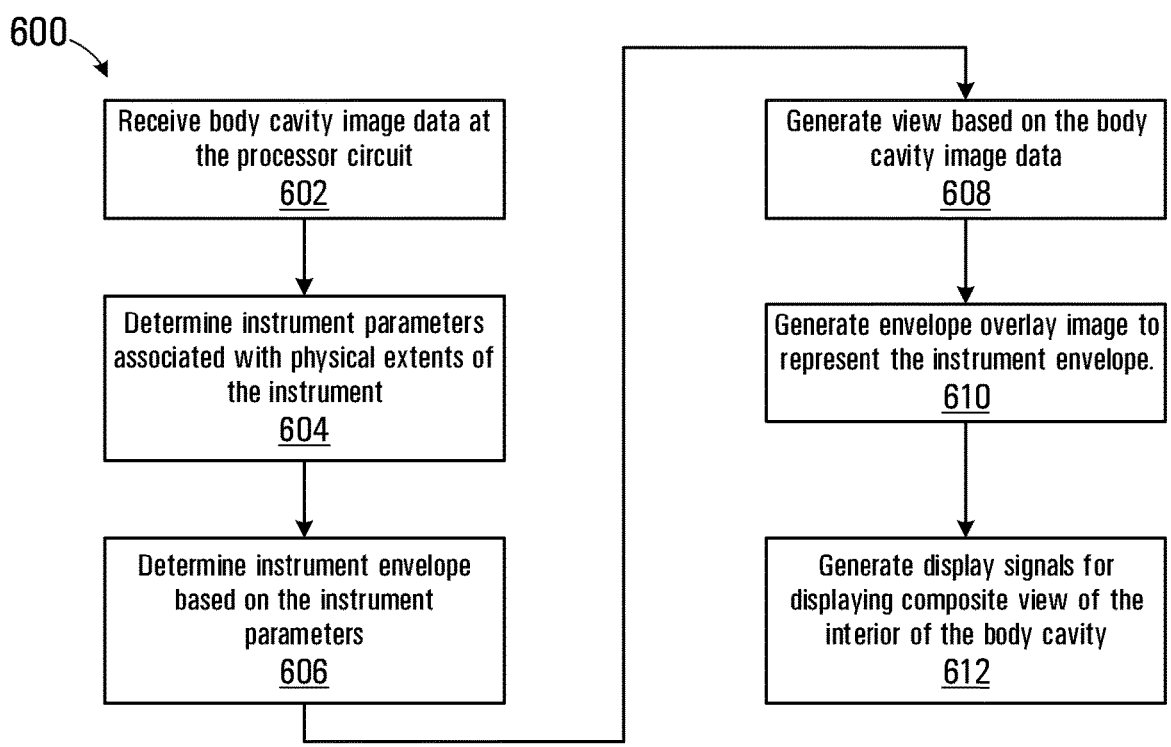
FIG. 6 is a flowchart depicting blocks of code for directing the processor circuit elements shown in FIG. 5 during insertion of an instrument into the body cavity of the patient's abdomen.

Referring to FIG. 6, a flowchart depicting blocks of code for directing the master and slave processor circuits 114 and 118 during insertion of an instrument into the body cavity 404 of the patient 400 is shown generally at 600. The blocks generally represent codes that may be read from the master processor memory 502 and slave processor memory 582 for directing the microprocessors 500 and 580 to perform various functions. The actual code to implement each block may be written in any suitable program language, such as C, C++, C#, Java, and/or assembly code, for example.

The process begins at block 602, which directs the microprocessor 580 of the slave processor circuit 118 to receive body cavity image data. The body cavity image data is captured by the camera 204 and represents an interior view of the body cavity 404. The insertion tube 108 may be moved around within the body cavity 404 to position the camera 204 to view various anatomical features within the body cavity 404. For example, in the embodiment shown in FIG. 4 the camera 204 is oriented to provide images of an ovary 414 of the patient 400. The body cavity image data is then relayed back via the interface cable 116 for receipt by the microprocessor 500 of the master processor circuit 114.

Block 604 then directs the microprocessor 500 of the master processor circuit 114 to determine instrument parameters associated with physical extents of the instrument to be inserted into the body cavity. In some embodiments each of the instruments 110 and 316 shown in FIG. 3, will have associated parameters that identify attributes of the instrument such its physical length, the type of end effector attached, offset in relation to the bore 300 and camera, actuation limits, etc. These parameters will generally have already been loaded into the memory 502 of the master processor circuit 114 in the instrument parameters memory location 522.

Block 606 then directs the microprocessor 500 to read the instrument parameters from the memory location 522 for each instrument and to determine an instrument envelope based on the instrument parameters. The instrument envelope corresponding to the instrument 110 is depicted in broken lines at 416 in FIGS. 4 and 5 and identifies a region through which the instrument 110 is capable of physically moving when inserted into the body cavity 404. Note that as shown in FIG. 4, the instrument 110 is not yet inserted through the insertion tube 108. Since the instrument 110 will be eventually inserted through the bore 300 of the insertion tube 108, the orientation of the instrument is determined by the orientation of the bore and the insertion tube. The instrument envelope 416 of the instrument 110 may have a generally cylindrical shape extending outwardly with respect to a longitudinal axis of the bore 300 and illustrates the potential reach of the instrument. The physical reach of the instrument 110 may be calculated as a length of the instrument when fully inserted in the bore 300, as defined in the instrument parameters memory location 522.

In some embodiments the instrument envelope 416 may represent a 3D volume, for example representing the total volume which may be occupied by the instrument when inserted through the insertion tube 108. In other embodiments the envelope may represent a physical reach of the instrument in at least one degree of freedom (for example along a longitudinal axis of the bore 300) associated with the instrument prior to insertion of the instrument into the body cavity.

Figure 7A:
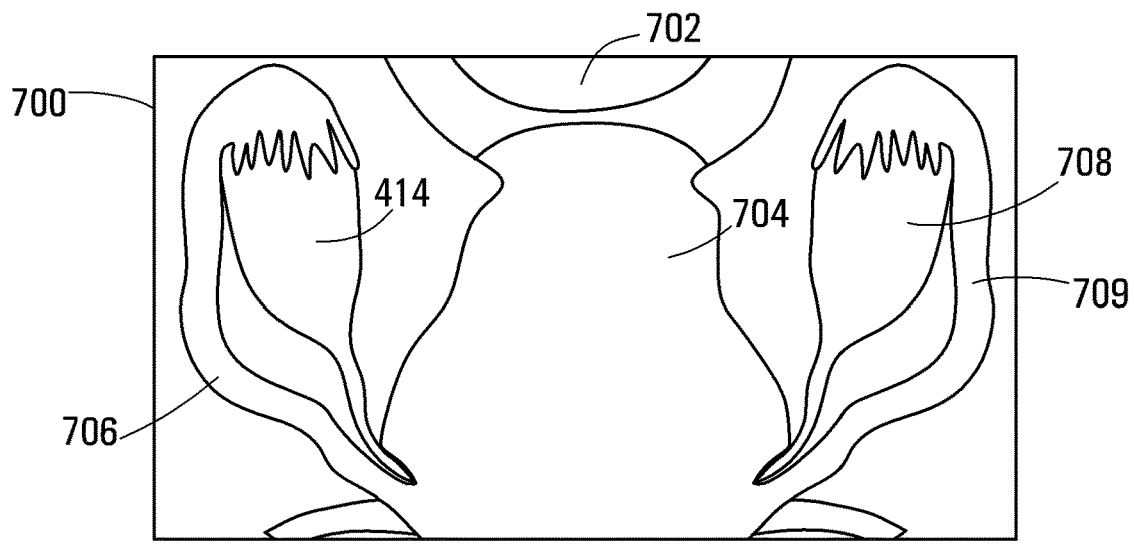
FIG. 7A is an example of an image represented by body cavity image data captured by the camera shown in FIG. 3A.

Block 608 then directs the microprocessor 500 to generate a view based on the body cavity image data being captured in real-time from the camera 204. The view thus represents current conditions within the body cavity 404. An example of an image represented by the body cavity image data is depicted in FIG. 7A at 700. The camera 204 captures an image within a field of view illuminated by the illumination source 308, in this case including the left ovary 414, a portion of the colon 702, the uterus 704, the left fallopian tube 706, as well as the right ovary 708 and right fallopian tube 709. The In some embodiments the body cavity image data may be streamed from the camera 204 as a real-time sequence of high-definition (HD) video frames for viewing as either 2D or 3D video on the display 120. To display 3D images, the master processor circuit 114 would need to be capable of generating the 3D point cloud, determining the instrument envelope, and generating the necessary projections at a reasonable frame rate (for example at 15-30 frames per second for HD video data).

Figure 7B:
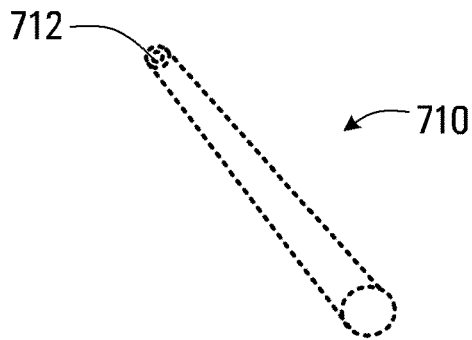
FIG. 7B is an example of an overlay image generated by the processor circuit elements shown in FIG. 5.

Block 610 then directs the microprocessor 500 to generate a view including an envelope overlay image representing the determined instrument envelope 416. The view generated at block 610 represents a prediction of the physical extents of the instrument 110 prior to the instrument actually being inserted into the body cavity. An example overlay image is shown in FIG. 7B at 710. In this embodiment the instrument is represented by a cylindrical shape shown as would appear from the perspective of the camera 204 with a distal end 712 representing the end effector.

Figure 14A:
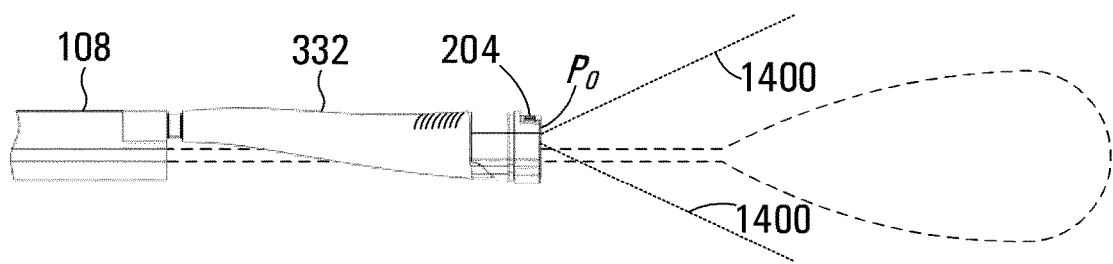
FIG. 14A is a side view of the insertion tube and instruments in an insertion position.

Referring to FIG. 14A, the camera 204 is shown longitudinally extended for initial positioning of the insertion tube 108 prior to inserting instruments through the insertion tube. The camera captures a view (indicated within the broken lines 1400) of the body cavity 404 from the perspective of the camera 204 when longitudinally extended and located in at the position $P_0$ before being moved into the deployed state (as shown at $P_1$ in FIG. 14B).

Figure 14B:
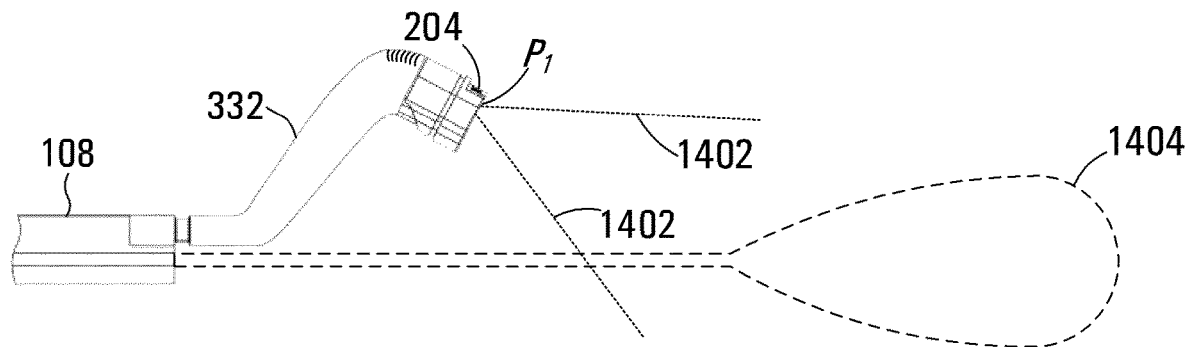
FIG. 14B is a perspective view of the insertion tube and instruments with the camera in a deployed state.

Referring to FIG. 14B, the camera 204 is shown oriented in the deployed state, which would be used for viewing of the body cavity 404 during a surgical procedure. In the deployed state the camera 204 is moved upwardly and angled down to provide a view 1402 of the surgical workspace within which the instruments are capable of reaching (shown in broken outline at 1404) and to facilitate insertion of the instruments through the insertion tube 108 and subsequent manipulation thereof. The view 1400 in FIG. 14A thus differs in perspective from the view in FIG. 14B due to the different positioning $P_0$ and $P_1$.

Figure 15A:
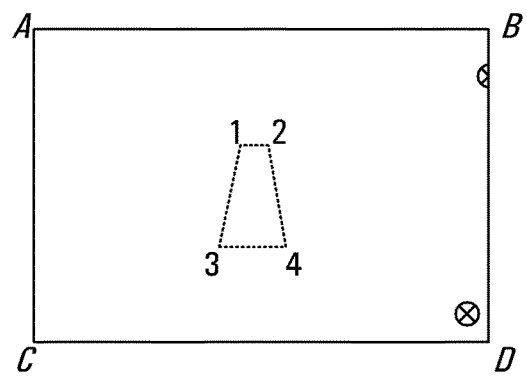
FIG. 15A is an example of a view captured by the camera in the position shown in FIG. 14A.
Figure 15B:
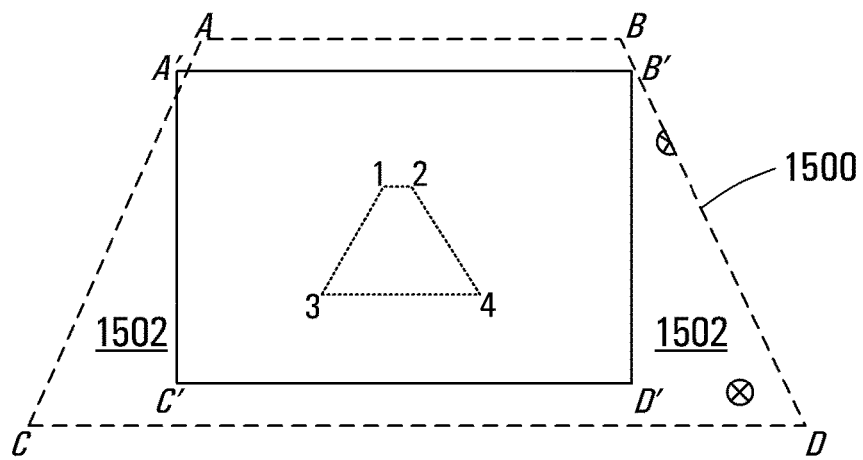

In some embodiments, the master processor circuit 114 is configured to distort the image captured by the camera 204 when in the position $P_0$ prior to display on the display 120. The degree of distortion of the image is selected to make the displayed image appear as if it were captured by the camera 204 in the deployed state $P_1$ so that the system 100 provides the surgeon with a displayed perspective that corresponds to the perspective displayed during the remainder of the surgical procedure once the camera 204 is deployed. The coordinates of the positions $P_0$ and $P_1$ may be determined based on parameters associated with actuation of the articulated arm 322. When the camera 204 is in the longitudinally extended state at position $P_0$ the image is distorted with respect to the image captured in the position $P_1$. An example of the image generated for the position $P_0$ of the camera 204 is shown in FIG. 15A and the boundaries of the display 120 or other display window are indicated as a rectangle ABCD. The image captured by the camera 204 at $P_0$ may be distorted to generate an acute trapezoid as shown in FIG. 15B at 1500. Since the distorted image 1500 no longer corresponds with the boundaries of the display 120 (i.e. A, B, C, D), the distorted image would need to be scaled to fit within the display boundaries ABCD. This results in some truncation of the originally captured image as shown at 1502 in FIG. 15B. The distorted image may be formed using the image provided by one of the stereoscopic imagers of the camera 204. A 2D representation of the envelope overlay images may then be displayed over the distorted image. Since only the perspective from a fixed and known position $P_1$ is required, generation of the distorted image may be based on a fixed distortion filter (i.e. a trapezoid distortion with parameters corresponding to the difference between the camera positions $P_0$ and $P_1$). The generation of the image would thus not be processor intensive since complex image transformation is not required. The estimation of the distorted view would thus produce a 2D image and a 2D representation of the envelope overlay images would accordingly be used when forming a composite image.

Although it may be beneficial to articulate the camera 204 from position $P_0$ to $P_1$ while the insertion tube 108 is being positioned to provide a "birds-eye" (from the perspective of the camera in a deployed state during surgery) view of the surgical site, it may not be possible as the camera may only be moveable when the insertion tube 108 is coupled to the drive unit 106, as described above. Estimation of the bird's eye view based on images captured while in the longitudinally extended state shown in FIG. 14A may thus be of use.

Figure 7C:
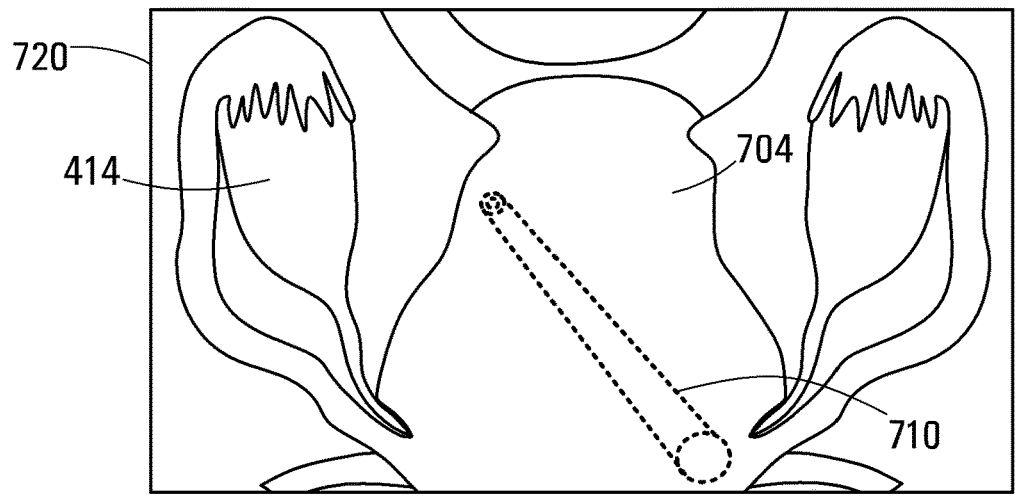
FIG. 7C is an example of a composite view generated by the processor circuit elements shown in FIG. 5.

The process 600 then continues at block 612, which directs the microprocessor 500 to generate display signals operable to display a composite view of the interior of the body cavity on the display 120 associated with the workstation 102. An example composite view is shown in FIG. 7C at 720 and is based on the body cavity image data captured by the camera 204 and includes the envelope overlay image 710. The composite view 720 illustrates the relative proximity between the instrument 110 and anatomy such as the uterus 704 and ovary 414 for the current camera position. In some embodiments the body cavity image 700 and envelope overlay image 710 may be generated at video frame rates in near-real time so that the display on the display 120 is continually updated as the insertion tube 108 is moved within the body cavity 404.

In other embodiments the envelope overlay image 710 may be displayed as a shaded region or other representation of the instrument envelope. Since the envelope overlay image 710 is based on physical parameters of the actual instrument 110, the composite view 720 thus provides a prior indication of an extent that the instrument will have, once inserted through the insertion tube 108 into the body cavity 404.

Referring to back to FIGS. 1, 3A and 4, in some embodiments, the display 120 may be capable of displaying the stereoscopic images for viewing through a pair of 3D viewing spectacles to provide a 3D view of the interior of the body cavity 404. For example, the captured 2D images produced by each of the pair of spaced apart imagers 304 and 306 may be presented in a format suitable for viewing with spectacles having colored filters, polarization filters, or actively shuttered spectacles. Alternatively, the display may be configured to display each image only to one of the operator's eyes using separate displays in a head mounted display.

In some embodiments, other 3D image capture techniques may be used to generate data having 3D information. For example, a time of flight camera may be used to generate image data including three-dimensional spatial information obtained on a pixel-by-pixel basis by determining the time that controlled illumination takes to be reflected back from anatomical features. Alternatively, a camera in combination with a structured light source for illuminating the interior of the body cavity may be used to facilitate determination of three-dimensional spatial information.

Figure 8:
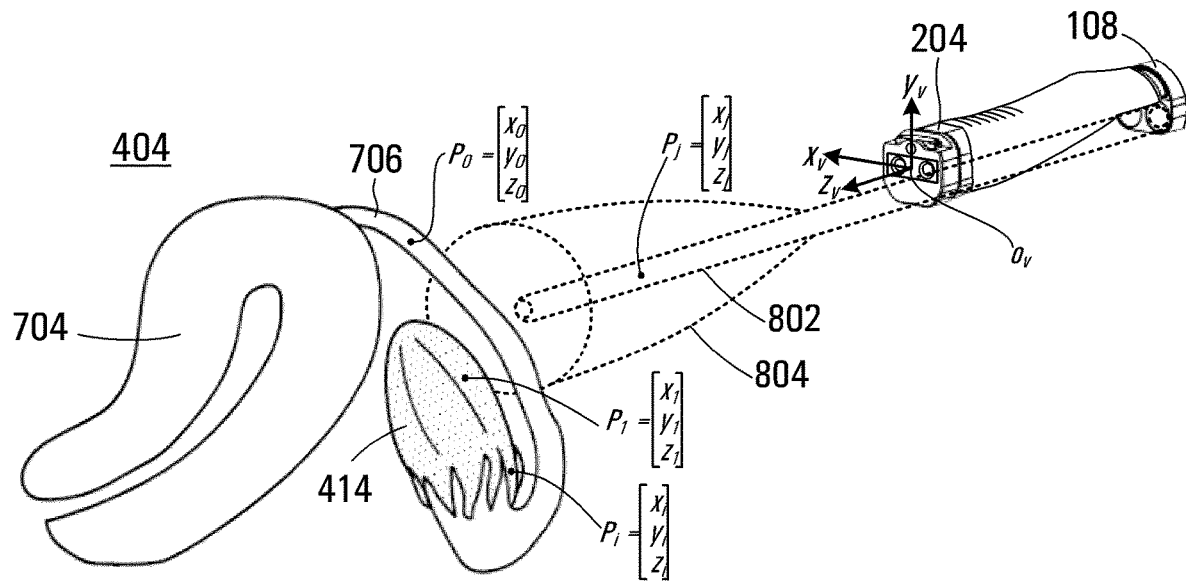
FIG. 8 is a further perspective view of the camera shown in FIG. 3A in relation to anatomy of the patient shown in FIG. 4.

Referring to FIG. 8, in some embodiments disclosed herein, the camera 204 includes the pair of spaced apart imagers 304 and 306 (shown in FIG. 3A) and each image sensor is operably configured to capture an image of the interior of the body cavity 404 from a different perspective within a coordinate frame $[x_v, y_v, z_v]$. In this embodiment the coordinate frame $[x_v, y_v, z_v]$ has an origin $o_v$ located at a center of the camera 204. In other embodiments, the origin of the coordinate frame may be located elsewhere on the insertion tube 108. The 2D images produced by the imagers 304 and 306 may be processed to generate a 3D point cloud using various open source or propriety library functions. The point cloud represents a set of points $P_i$, such as the points $P_0$ and $P_1$ shown in FIG. 8. The point cloud points $P_i$ are generated from the 2D images by determining a distance between common points on the surface as represented by the separate images produced by the spaced apart imagers 304 and 306. Generation of the point cloud thus provides 3D coordinates within the coordinate frame $[x_v, y_v, z_v]$ of points $P_i$ representing surfaces of anatomical features such as the ovary 414, uterus 704, and fallopian tube 706.

The instrument parameters stored in the memory location 522 of the master processor memory 502 are then used to determine the range of possible motion of the instrument 110 with respect to the bore 300 within the coordinate frame $[x_v, y_v, z_v]$. For example, the instrument parameters 522 may include a maximum distance between an opening of the bore 300 and the end effector 312 of the instrument 110 when the instrument is fully inserted and advanced through the bore. The instrument parameters 522 may further include an offset distance between the opening of the bore 300 and the origin of the coordinate frame $[x_v, y_v, z_v]$ at the camera 204. These parameters may be used, along with an outside diameter of the instrument 110, to generate the instrument envelope 802 (shown in broken lines) within the coordinate frame $[x_v, y_v, z_v]$. The extent of the cylindrical instrument envelope 802 may then be converted into a point cloud of points $P_j$ or may be represented other 3D representation techniques, such as a polygon mesh (not shown) having vertices located on the surface of the cylindrical volume.

In some embodiments, the instrument parameters 522 may also include articulation information defining a manipulation region within which the manipulator 310 (shown in FIG. 3C) is capable of moving the end effector 312. In some embodiments the cylindrical instrument envelope 802 may be further expanded to include the manipulation region that the instrument 110 will have once inserted. The instrument envelope may thus be displayed as an outline of a volume 804 demarcating extents for manipulation of the instrument in response to movements of the input device 112 (shown in FIG. 1). The shape of the volume 804 is dependent on the type of manipulator 310 that is implemented to provide the dexterous movement of the instrument 110.

A listing of typical instrument parameters that may be saved in the instrument parameters memory location 522 are listed in Table 1 below.

TABLE 1

| | |
|---|---|
| $q_{ins}$ | z-position of the insertion tube |
| $\theta_1$ | Angle that represents how much the s-segment is bent |
| $\delta_1$ | Angle that represents the plane in which the s-segment is bent. |
| $\theta_2$ | Angle that represents how much the distal segment is bent |
| $\delta_1$ | Angle that represents the plane in which the distal segment is bent. |
| $\gamma$ | Wrist roll |

Generation of the envelope overlay image 710 may involve generating 3D image data in a similar format to the image data produced by the camera 204 to facilitate generation of a 3D composite view 720 by overlaying the instrument envelope image over the body cavity image data. For the example of a stereoscopic image display, the microprocessor 500 may be operably configured to generate projections of a 3D envelope overlay image 710 onto 2D planes corresponding to the body cavity images generated by the pair of spaced apart imagers 304 and 306. The resulting 2D envelope projections may then be combined with the original body cavity images as an overlay image to produce a 3D view of the envelope overlay image 710 within a 3D composite view. In some embodiment, the overlay image may be displayed as a shaded or a semi-transparent 3D region in the resulting 3D composite view. In other embodiments the overlay image may be displayed showing only an outline of the instrument envelope. Standard open source image overlay functions are generally available for performing a combination of two or more images and may be used to implement the process in near real time.

Figure 16:
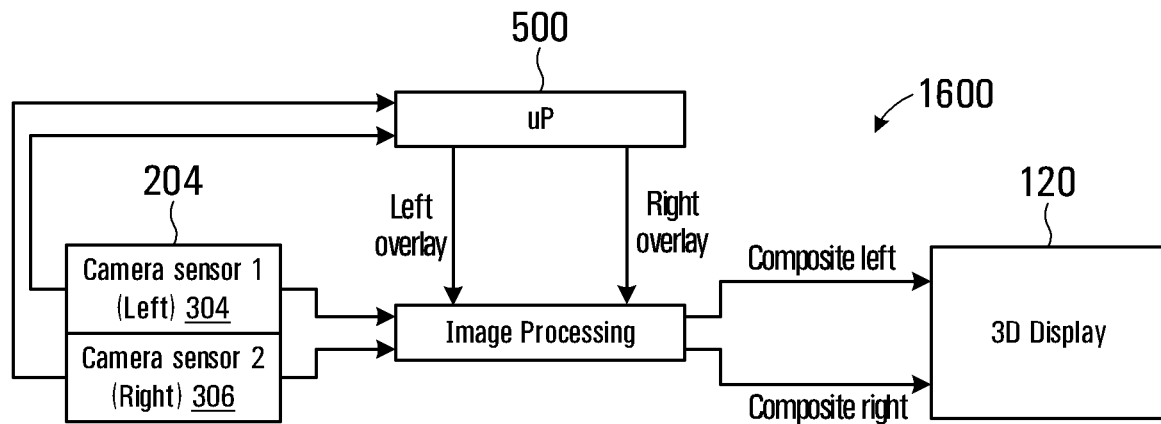
FIG. 16 is a block diagram of processor circuit elements involved in generation of a 3D composite view.

Referring to FIG. 16, a block diagram illustrating the processing and generation of signals by the microprocessor 500 for producing the 3D composite view is shown at 1600. The microprocessor 500 of the master processor circuit 114 receives left and right images from the spaced apart left and right imagers 304 and 306 of the camera 204 and generates a 3D point cloud. An available software tool such as OpenGL may be implemented on the microprocessor 500 to render a 3D scene of the point cloud as well as the 3D envelope overlay. The 3D point cloud and 3D envelope are rendered together so that the 3D envelope is clipped where it intersects the point cloud. The known position of the camera in relation to the z-axis the insertion tube 108 (shown in FIG. 3A) may then be used to create two views; one view for the left imager and another view for the right imager. Finally, the left and right views are rendered without the point cloud and output to the image processing block, which creates the left and right composite views.

In the embodiment shown, the insertion tube 108 and camera 204 are initially detached from the drive interface 202 of the drive unit 106, facilitating positioning of the camera by hand to receive a desired interior view of the body cavity 404 based on the composite view. Once the camera 204 is positioned to provide the desired view, based on the composite view, the operator ensures that the insertion tube 108 is located such that the instrument 110 can be safely inserted and once inserted will be disposed to provide an adequate range of manipulation for performing the desired surgical process. The drive unit may then be connected to the drive unit 106 and further positioning of the camera 204, such as for example moving to the deployed state shown in FIG. 3C, may then be performed under control of the master processor circuit 114 and slave processor circuit 118. Following the actual insertion of the instrument 110 through the bore 300 of the insertion tube 108 into the body cavity 404, the microprocessor 500 of the master processor circuit 114 may be directed to discontinue display of the envelope overlay image, since the instrument 110 would then move into the view in place of the instrument envelope.

In some embodiments, the insertion tube 108 once coupled to the drive interface 202 of the drive unit 106 may need to be repositioned for various reasons, including a need to adjust the available surgical workspace that is within reach of the manipulation range of the instruments 110 and second instrument 316. When the insertion tube 108 is coupled to the drive interface 202, repositioning of the insertion tube may be accomplished by repositioning the drive unit 106 manually (by a bed side nurse or surgeon other than the surgeon operating the workstation 102). Alternatively, the surgeon operating the workstation 102 may generate actuation signals at the workstation 102 (for example by moving the hand controllers 122) to cause the insertion tube 108 to be repositioned. In either case, the system 100 may be first configured to decouple the instruments 110 and 316 and/or camera 204 from the input device 112 so that further movement within the body cavity 404 is inhibited. For example, decoupling of the instruments 110 and 316 may be caused by the surgeon depressing a clutch pedal 126 that prevents further changes to the instrument actuation signals such that the instrument cart 104 inhibits further movements that could cause damage to the patient's tissues or organs.

Figure 9:
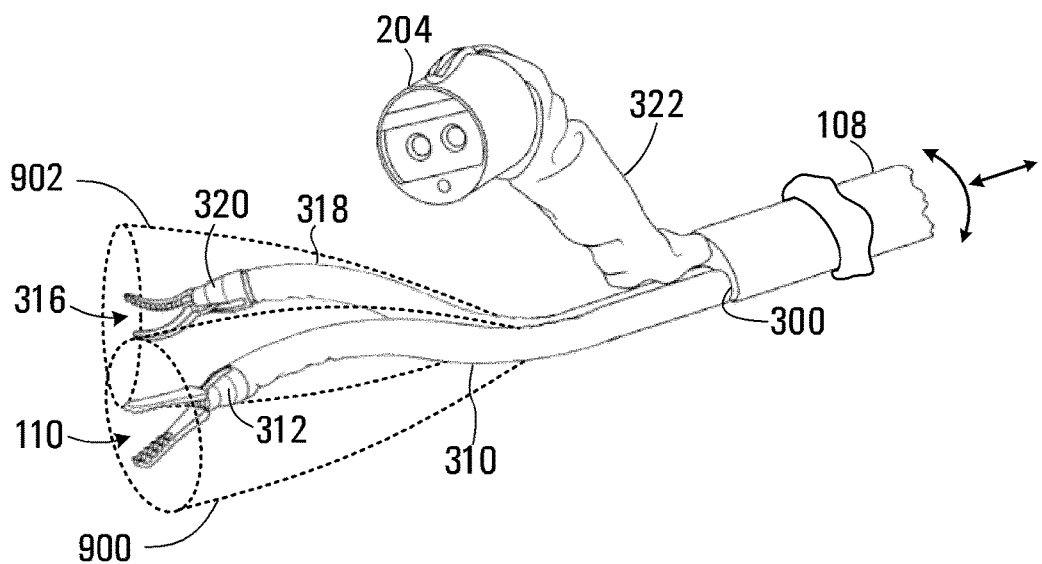
FIG. 9 is a perspective view of a deployed camera and instruments in accordance with some embodiments.
Figure 10:
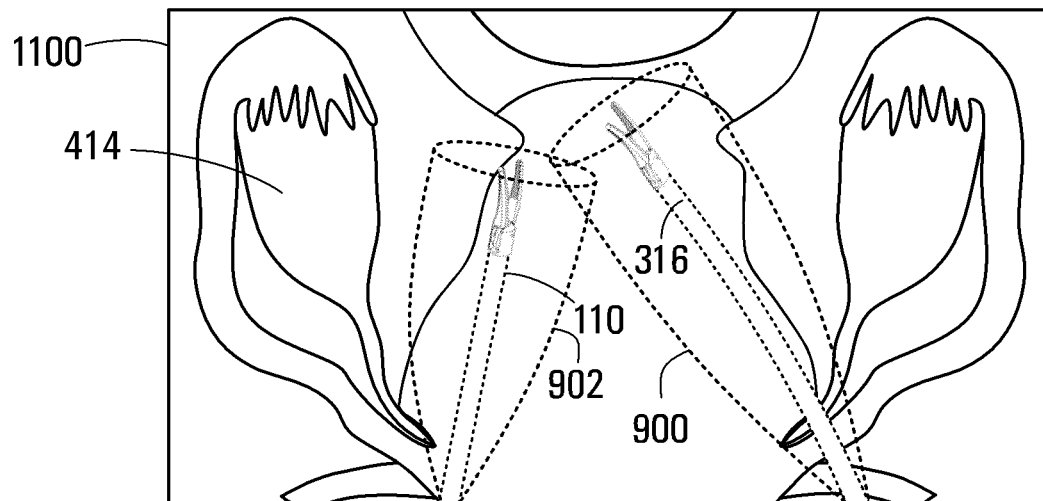
FIG. 10 is a generated composite view corresponding to the deployed camera and instruments shown in FIG. 9.

Referring to FIG. 9, in the embodiment shown, when in the decoupled state instrument envelope overlay images 900 and 902 (similar to that shown at 804 in FIG. 8) may be generated and displayed for each of the instruments 110 and 316 to indicate the respective instrument manipulation regions while repositioning of the insertion tube 108 to a safe and desired position. Referring to FIG. 10, a resulting composite view of the instrument envelope overlay images 900 and 902 as viewed on the display 120 (from the perspective of the camera 204) is shown at 1000. The composite view 1000 depicted in FIG. 10 is a "birds-eye" view from the view point of the camera 204 in its deployed state as shown in FIG. 9. While decoupled, movement of the instruments 316 and 110 will be inhibited by the instrument cart 104. However the surgeon operating the workstation 102 will be able to generate input signals (for example using the hand controllers 122 and 124 of the input device 112) to reposition the camera and/or the instruments to better facilitate surgical operations within the body cavity 404. The composite view 1000 thus depicts the possible range of manipulation 900 and 902 for each of the instruments 316 and 110 and provides information to aid in the repositioning.

Figure 11:
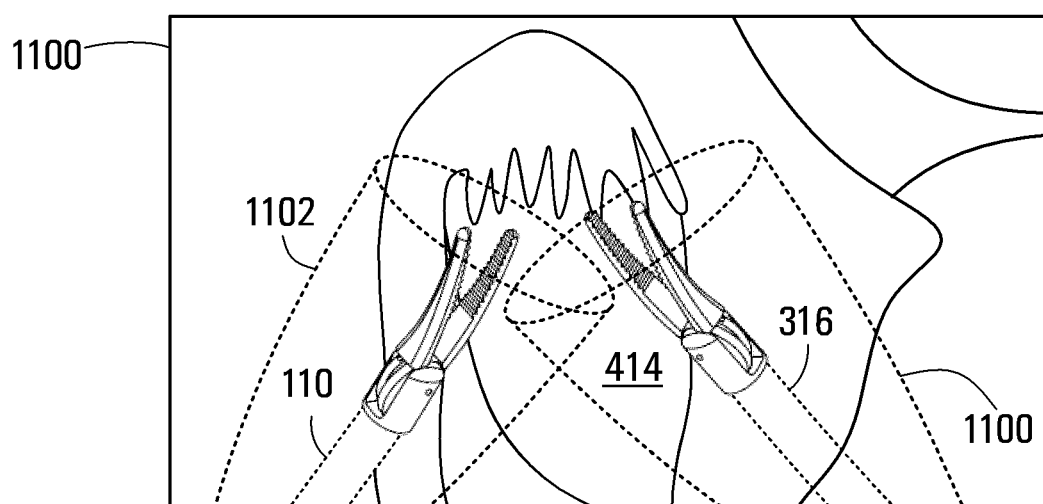
FIG. 11 is another generated composite view corresponding to the deployed camera and instruments shown in FIG. 9.

Referring to FIG. 11, as a further example, the surgeon may wish to perform surgical operations in a specific anatomical region such as the ovary 414. In this case, a composite view 1100 may display an enlarged portion of the patient's anatomy along with the instrument envelope overlay images 1100 and 1102 depicting the associated possible range of manipulation of the instruments 110 and 316.

Figure 12:
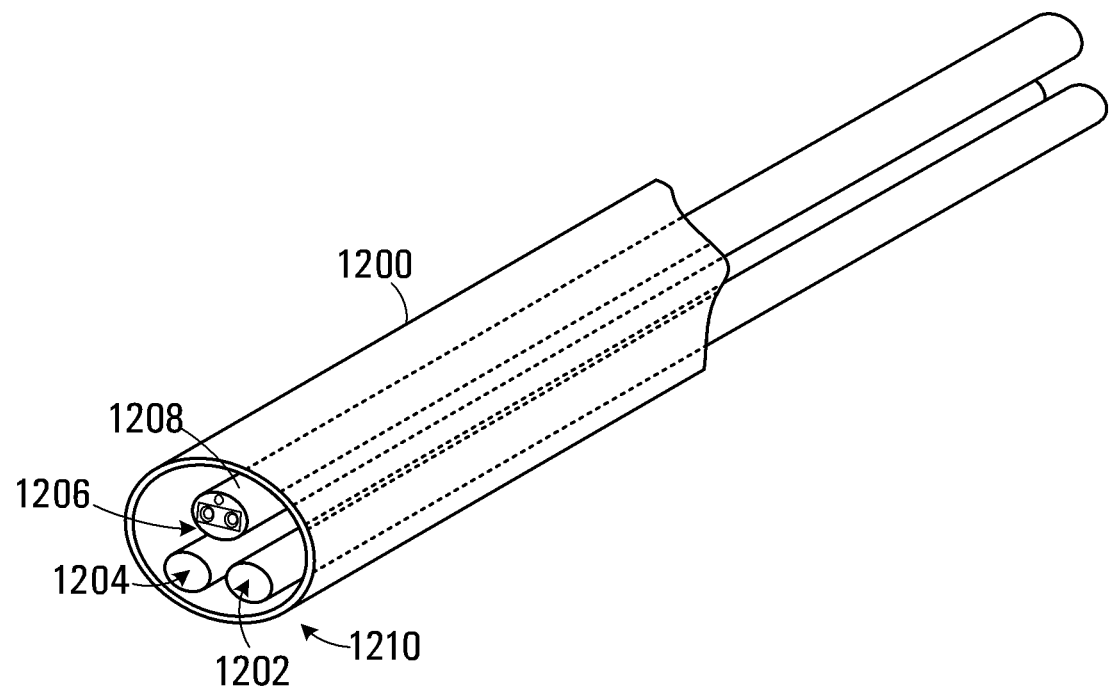
FIG. 12 is a perspective view of a portion of an insertion tube in accordance with some embodiments.

In some embodiments disclosed herein, the camera 204 is integrally coupled to and part of the insertion tube 108. In other embodiments, the camera may be received as a separate unit in an insertion tube. For example, referring to FIG. 12, an insertion tube 1200 is sized to permit first and second instruments 1202 and 1204 and a camera 1206 to be received. The camera 1206 is configured as a separate unit having its own sheath 1208. The insertion tube 1200 may still be inserted through the opening 410 in the cap 408 (FIG. 4) or other body orifice. The camera 1206 and first and second instruments 1202 and 1204 are all independently movable through the insertion tube 1200. In other embodiments (not shown) the insertion tube 1200 may have separated bores for accommodating the camera 1206, and each of the first and second instruments 1202 and 1204. In some embodiment the insertion tube 1200 may be inserted partway into the body cavity 404 through the opening 410 before the camera 1206 and instruments 1202 and 1204 are inserted. Subsequently, when the camera 1206 is inserted and reaches an end 1210 of the insertion tube 1200 the composite images depicting instrument envelopes similar to those shown in FIGS. 9 to 11 may be generated to allow the insertion tube to be positioned appropriately, as generally disclosed above. Once the insertion tube 1200 has been positioned with the aid of the composite images generated by the camera 1206 and system, the instruments 1202 and 1204 can be inserted and would move into view in place of the respective instrument envelopes.

In some robotic surgery systems, the camera and instruments are independently movable and may be inserted through separate incisions. For example, a camera may be coupled to a first manipulator associated with a robotic surgery system and an instrument may be coupled to a second manipulator, both of which are independently moveable. In this case, the location of the instrument will not be constrained by an instrument bore (as in the case of the bore 300 of the insertion tube 108) but rather by the point at the incision through which the instrument is inserted into the body cavity. It would then be necessary to first determine a spatial disposition of the camera and then determine the anticipated insertion location and orientation for the instrument by receiving kinematic information associated with the first and second manipulators and determining the anticipated insertion location and orientation for the instrument as offsets from the respective orientations and locations of the first and second manipulators. The instrument parameters 522 may then be used to determine the possible physical extent of the instrument within the body cavity 404.

Figure 13:
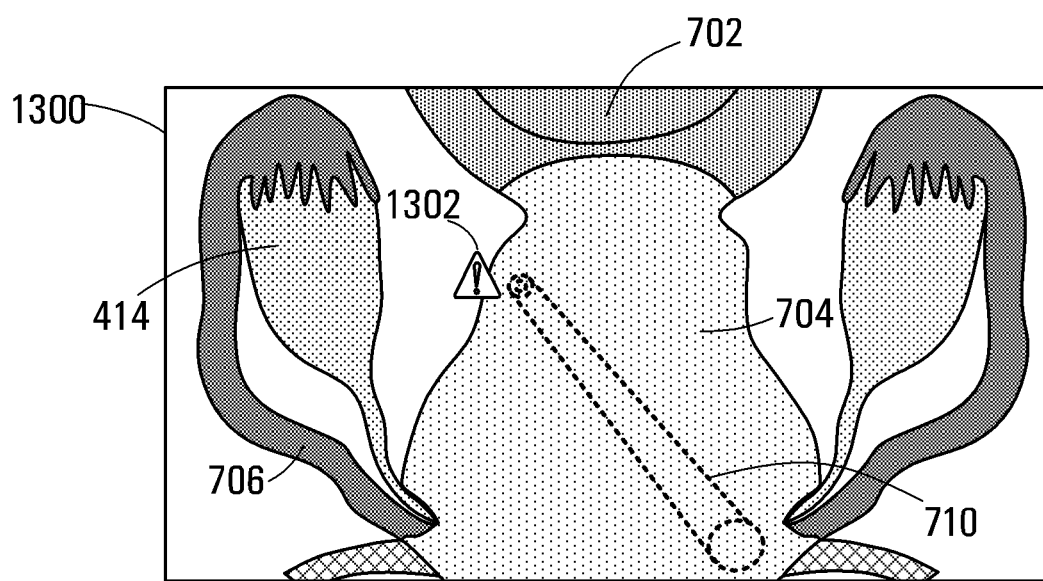
FIG. 13 is a further example of a composite view generated by the processor circuit elements shown in FIG. 5.

Referring to FIG. 13, in some embodiment the body cavity image data may be processed by the master processor circuit 114 to identify anatomical features within a composite view as shown generally at 1300. For example, the master processor circuit 114 may be operably configured to identify major organs such as the ovary 414, uterus 704, colon 702, etc. In one implementation, the master processor circuit 114 may implement machine-learning techniques to train an image recognition algorithm to recognize anatomical features under various conditions. The image recognition algorithm may be neural network based and may be trained using a set of labeled training images in which features such as the fallopian tube 706, and ovary 414 have been previously manually labeled by an operator.

When generating the composite view 900, an additional overlay image identifying at least one anatomical feature within the body cavity 404 may be generated. The composite view 1300, in addition to the body cavity image 700 and envelope overlay image 710 (shown in FIG. 7) may also include highlighting or other overlay identifying some anatomical features. For example, relevant anatomical features in the composite view 1300 may be displayed together with shading or semi-transparent overlay colors to indicate different anatomical features. In some embodiments, the master processor circuit 114 may determine whether there are any regions of potential encroachment of between the instrument envelope 710 and an identified anatomical feature, in which case an alert signal may be generated. The alert signal may take the form of a further warning overlay image 1302 for display as part of the composite image. The warning overlay image 1302 may also be accompanied by an audible warning or by haptic feedback via the input device 112. Alternatively, the alert signal may further be transmitted to the slave processor circuit 118 to cause the drive unit 106 to generate drive signals that limit further movement of the drive unit 106 and the insertion tube 108 to prevent or otherwise limit full movement of the camera and/or instruments into the region of potential encroachment. A similar alert signal may also be generated when repositioning the insertion tube 108 to highlight a potential encroachment of between the instrument envelope and an identified anatomical feature. Repositioning of the insertion tube 108 may involve causing the insertion tube to pivot about the location of the incision or causing a portion of the insertion tube to articulate along its length to reposition a distal end of the insertion tube.

Generation of the overlay image for highlighting the anatomical features may involve the master processor circuit 114 processing the body cavity image data using the image recognition algorithm to identify surface regions associated with the anatomy in the area of the surgical worksite. Each surface region may then be represented using a polygon mesh representation or other method. A similar polygon mesh representation may also be generated for the envelope overlay image 710 and points of proximity or intersection between the instrument envelope and the anatomy surface region may be determined. Standard 3D surface intersection library functions for this purpose are available in open source libraries of functions.

Figure 17:
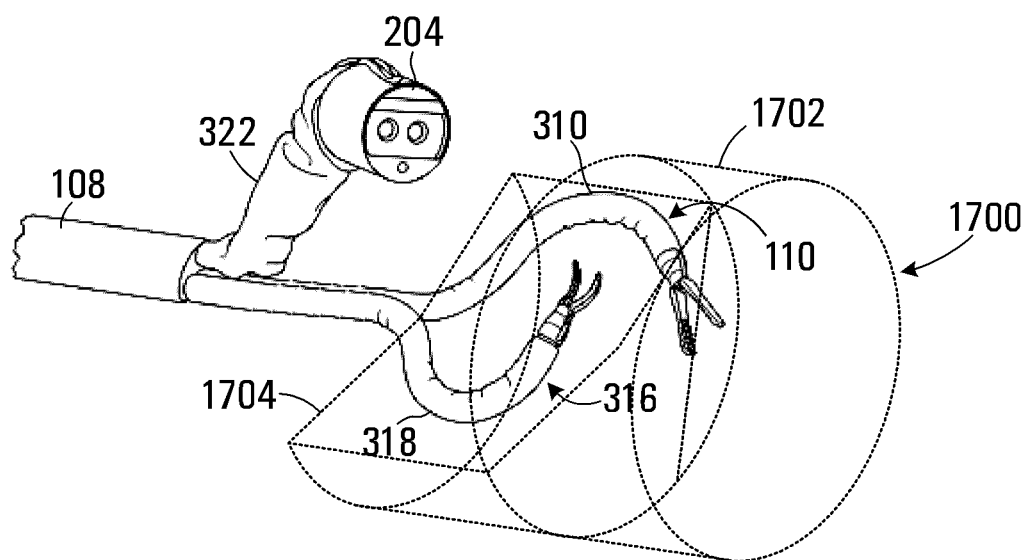
FIG. 17 is a perspective view of a camera and insertion tube and an overlay image generated in accordance with some embodiments.
Figure 18:
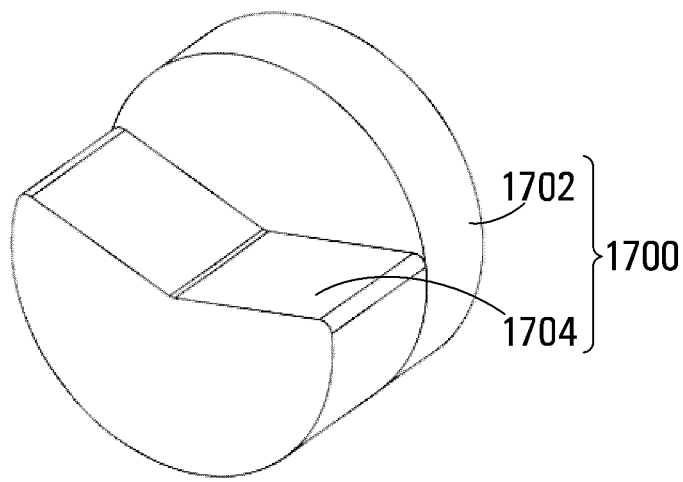
FIG. 18 is a perspective view of the overlay shown in FIG. 18 from a different perspective viewpoint.

Referring to FIG. 17, in another embodiment the overlay image may be generated as a 3D volume reachable by manipulating the instruments 110 and 316, as shown at 1700 in broken lines. The volume 1700 has a first portion 1702 within which the instruments 110 and 316 are freely able to move within the constraints provided by the manipulators 310 and 318. The volume 1700 has a second portion 1704 proximate the insertion tube 108 that may be encumbered by the camera 204, even when in the deployed state. A non-manipulatable portion of the instruments 110 and 316 proximate the insertion tube 108 may also have a role in determining the second portion 1704. A remaining workable volume is thus enclosed within the volume 1700, which may be displayed on the display 120 to indicate this workable volume. The workable volume is the region where the end-effectors can reach by manipulating the instruments 110 and 316 and moving the instruments in the z-axis direction. The workable volume 1700 would thus be dependent on the deployed position of the camera 204 and the articulated arm 322 supporting the camera, and also on the structure of the instruments 110 and 316. The workable volume 1700 is shown from a different perspective in FIG. 18. In some embodiments the first portion 1702 and second portion 1704 may be otherwise shaped depending on the structural features of the insertion tube 108, camera 204, and the instruments 110 and 316. The workable volume 1700 may be generated based on the instrument parameters as described above.

The above disclosed embodiments provide a representation of the instrument prior to actual insertion into the patient and thus prevent inadvertent damage to tissue or organs of the patient. The surgeon or other operator is able to safely view the interior of the body cavity and position the camera to capture images of the surgical worksite. The generated composite view including the overlay image provides a visual cue to the surgeon of possible engagement between the instrument and sensitive anatomy, thus facilitating positioning of the camera prior to insertion of the instrument.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

While specific embodiments have been described and illustrated, such embodiments should be considered illustrative only and not as limiting the disclosed embodiments as construed in accordance with the accompanying claims. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

What is claimed is:

1. A method of assisting positioning of an instrument in a body cavity of a patient to perform a surgical procedure using a robotic surgery system, the robotic surgery system being controlled by a processor, the method comprising, by the processor:

receiving body cavity image data representing an interior view of the body cavity, the body cavity image data being captured by a camera inserted into the body cavity;

processing the body cavity image data to identify at least one anatomical feature;

generating one or more display signals configured to display a composite view of the interior view of the body cavity on a display associated with the robotic surgery system, the composite view being at least partially based on the body cavity image data and including at least one anatomical overlay image being configured to identify the at least one anatomical feature;

determining an instrument envelope identifying a workable volume of the instrument, the workable volume comprising a possible range of motion of the instrument within the body cavity; and causing display of the composite view, the composite view comprising an envelope overlay image being configured to represent the instrument envelope.

2. The method of claim 1, wherein the at least one anatomical overlay image comprises a highlighted region within the body cavity image data, and wherein the highlighted region is configured to identify at least a portion of the at least one anatomical feature.

3. The method of claim 1, wherein determining the instrument envelope is further at least partially based on processing the body cavity image data to determine the instrument envelope at least partially based on determining an anticipated position of the instrument relative to the camera.

4. The method of claim 3, wherein the camera is coupled to a first manipulator and the instrument is coupled to a second manipulator, wherein each of the first and second manipulators is associated with the robotic surgery system, and wherein the method further comprises:

determining a spatial disposition of the camera;

determining the anticipated position of the instrument by receiving kinematic information associated with the first and second manipulators; and determining the anticipated position of the instrument as offset from a respective position of each of the first and second manipulators.

5. The method of claim 1, wherein the method further comprises causing discontinuing display of the envelope overlay image following actual positioning of the instrument.

6. The method of claim 1, further comprising:
    determining a region of potential encroachment between the instrument envelope and at least one of the identified at least one anatomical feature; and
    generating an alert in response to identifying a region of potential encroachment.

7. The method of claim 6, wherein the alert comprises a warning overlay image configured to be displayed as part of the composite view.

8. The method of claim 6, wherein the camera is coupled to a drive unit configured to move the camera within the body cavity, and wherein the method further comprises inhibiting further movement of the drive unit in response to the alert.

9. The method of claim 1, wherein the camera is configured to detach from the robotic surgery system to facilitate positioning of the camera by hand and to receive a desired interior view of the body cavity at least partially based on the composite view, and wherein the method further comprises:
    positioning the camera; and
    after positioning the camera, connecting the camera to the robotic surgery system to facilitate further positioning of the camera by the processor.

10. A robotic surgery system comprising:
    a camera being configured to be inserted and positioned in a body cavity of a patient, the camera being further configured to capture body cavity image data representing an interior view of the body cavity; and
    a processor being configured to control the robotic surgery system, the processor being further configured to:
        receive the body cavity image data;
        process the body cavity image data to identify at least one anatomical feature;
        generate display data being configured to cause a display to display a composite view of the interior view of the body cavity, the composite view being at least partially based on the body cavity image data and including at least one anatomical overlay image configured to identify the at least one anatomical feature within the body cavity; and
        determine an instrument envelope identifying a workable volume of an instrument, the workable volume comprising a possible range of motion of the instrument within the body cavity,
    wherein the display is configured to receive the display data and to display the composite view at least partially based on the display data, the composite view comprising an envelope overlay image being configured to represent the instrument envelope.

11. The system of claim 10, wherein the at least one anatomical overlay image comprises a highlighted region within the body cavity image data, and wherein the highlighted region is configured to identify at least a portion of the at least one anatomical feature.

12. The system of claim 10, wherein the system further comprises the instrument, and wherein the instrument is configured to be inserted into and perform a surgical procedure within the body cavity when the instrument is received in the body cavity.

13. The system of claim 10, wherein the possible range of motion of the instrument corresponds to a physical extent of the instrument when the instrument is positioned within the body cavity.

14. The system of claim 12, wherein the processor is configured to cause the display to discontinue display of the envelope overlay image following actual positioning of the instrument.

15. The system of claim 12, wherein the processor is further configured to determine whether there are any regions of potential encroachment between the instrument envelope and at least one of the identified at least one anatomical feature and to generate an alert in response to identifying a region of potential encroachment.

16. The system of claim 15, wherein the alert comprises a warning overlay image configured to be displayed as part of the composite view.

17. The system of claim 15, wherein the camera is configured to be coupled to a drive unit configured to move the camera within the body cavity, and wherein the processor is further configured to inhibit further movement of the drive unit in response to the alert.

18. The system of claim 12, wherein the processor is configured to determine the instrument envelope at least partially based on determining an anticipated position of the instrument relative to the camera,
    wherein the camera is configured to be coupled to a first manipulator and the instrument is configured to be coupled to a second manipulator, wherein each of the first and second manipulators is associated with the robotic surgery system, and
    wherein the processor is further configured to:
        determine a spatial disposition of the camera; and
        determine the anticipated position of the instrument at least partially based on received kinematic information associated with the first and second manipulators to determine the anticipated position of the instrument as offset from a respective position of each of the first and second manipulators.

19. The system of claim 10, wherein the robotic surgery system is configured to permit the camera to be detached from the system to facilitate positioning of the camera by hand and to receive a desired interior view of the body cavity at least partially based on the composite view, and wherein the system is further configured to facilitate connecting the camera to the robotic surgery system once the camera is positioned to facilitate further positioning of the camera by the processor.

20. The method of claim 1, wherein the workable volume comprises a location in which the instrument is configured to be positioned within the body cavity.

21. The method of claim 1, wherein the possible range of motion of the instrument corresponds to a physical extent of the instrument when the instrument is positioned within the body cavity.

22. The system of claim 10, wherein the workable volume comprises a location in which the instrument is configured to be positioned within the body cavity.

23. The system of claim 13, wherein the processor is further configured to determine an instrument envelope at least partially based on at least one instrument parameter, and wherein the at least one instrument parameter provides information to determine the physical extent of the instrument when the instrument is positioned within the body cavity.

24. The method of claim 21, wherein determining the instrument envelope comprises determining at least one instrument parameter, and wherein the at least one instrument parameter provides information to determine the physical extent of the instrument when the instrument is positioned within the body cavity.

* * * * *